US 6,425,878 B1

(12) United States Patent
Shekalim

(10) Patent No.: US 6,425,878 B1
(45) Date of Patent: Jul. 30, 2002

(54) METHOD AND DEVICE FOR DETECTING EXTRAVASATION

(75) Inventor: Avraharn Shekalim, Nesher (IL)

(73) Assignee: L.G.MED Ltd., Migdal Haemek (IL)

( * ) Notice: Subject to any disclaimer, the term of this patent is extended or adjusted under 35 U.S.C. 154(b) by 0 days.

(21) Appl. No.: 09/793,882

(22) Filed: Feb. 28, 2001

(51) Int. Cl.$^7$ ................ A61M 31/00; A61B 5/05
(52) U.S. Cl. .............. 604/65; 604/66; 604/503; 600/384; 600/393
(58) Field of Search .................. 604/65, 66, 67, 604/503; 600/382, 549, 561, 384, 393, 372

(56) References Cited

U.S. PATENT DOCUMENTS

| | | | | |
|---|---|---|---|---|
| 3,618,602 A | * | 11/1971 | Shaw | 604/66 |
| 4,010,749 A | * | 3/1977 | Shaw | 604/503 |
| 4,877,034 A | * | 10/1989 | Atkins et al. | 600/475 |
| 5,334,141 A | * | 8/1994 | Carr et al. | 604/65 |
| 5,964,703 A | * | 10/1999 | Goodman et al. | 600/382 |

* cited by examiner

Primary Examiner—Patrick Brinson
(74) Attorney, Agent, or Firm—Mark M. Frieom

(57) ABSTRACT

A method and device for detecting extravasation employs a non-invasive sensor system deployed on the skin to identify changes in both subcutaneous interstitial fluid pressure and skin temperature. Preferably, the system monitors the sensor system outputs to identify a sequence of a skin temperature drop followed by a interstitial fluid pressure increase. This pattern is distinctive of the occurrence of extravasation, thereby providing very reliable detection. Most preferably, a simple sensor structure based upon multiple piezoelectric film sensors is used.

9 Claims, 7 Drawing Sheets

METHOD AND DEVICE FOR DETECTING EXTRAVASATION

FIELD AND BACKGROUND OF THE INVENTION

The present invention relates to detection of malfunction during intravascular delivery of fluids and, in particular, it concerns a method and device for detecting extravasation.

A common problem encountered in intravenous fluid administration is the infiltration of the fluids into tissues near the tip of the catheter. This phenomenon, variously referred to as "infiltration" and "extravasation", may occur through a number of different mechanisms, not all of which are completely understood, but is often due to patient movement and disruption of the vein or artery at the end of the catheter. Although some texts make certain distinctions between the terms infiltration and extravasation, they are widely used, and will be used herein, interchangeably to denote generically any and all circumstances in which intravenous fluid delivery spreads beyond the blood vessel to adjacent tissue. Extravasation may lead to discoloration, discomfort and tissue destruction as well as lack of delivery of the intravenous fluids or drugs into the patient's system. In the case of certain medications, infiltration of the drugs into the patient's tissues may be dangerous, causing necrosis or other serious damage, requiring surgical procedures such as amputation. Permanent disfigurement and/or disability may result.

A number of devices and methods have been proposed for detection of tissue infiltration during intravenous administration of fluids. A common method for detecting infiltration is by monitoring the rate of flow or pressure of fluid in the supply line. Examples of such devices are disclosed in U.S. Pat. No. 4,534,756 to Nelson, U.S. Pat. No. 4,784,648 to Singh et al., and U.S. Pat. No. 4,979,940 to Bobo, Jr. et al. Commercially available devices based on these techniques, however, are generally ineffective since the pressure differences indicative of extravasation are typically small in relation to other causes of pressure variations such as patient movements or changes in the head pressure of an infusion bag.

A second approach to detection of extravasation is based upon the measurement of the skin temperature in potential infiltration areas. These devices use temperature sensors for continuous monitoring of the skin temperature near the intravenous catheter. When colder intravenous fluids accumulate in tissue from infiltration the skin temperature falls. Examples of such devices may be found in U.S. Pat. No. 4,010,749 to Shaw and U.S. Pat. No. 4,378,808 to Lichtenstein. These devices do not work well when the administered fluid is not significantly colder than the patient's skin, when slow delivery rates are used, or when the patient's body temperature varies. Such devices are also highly susceptible to false alarms due to changes in ambient temperatures.

Additional examples of proposed techniques include measurements of conductivity (e.g. U.S. Pat. No. 5,964,703 to Goodman et al.) and measurements of spectral reflection (e.g. U.S. Pat. No. 4,877,034 to Atkins et al.).

Due to the cost and reliability limitations of the available devices, the predominant technique for identifying extravasation remains visual inspection by hospital personnel of the area surrounding the catheter for swelling or other signs of infiltration. To be effective this technique requires continual monitoring by trained hospital personnel.

There is therefore a need for a device and method for detecting extravasation of fluid into tissue surrounding a blood vessel into which the fluid is intended to be delivered.

SUMMARY OF THE INVENTION

The present invention is a method and device for detecting extravasation.

According to the teachings of the present invention there is provided, a method for detecting extravasation of a fluid delivered from the tip of a catheter into tissue located under a first region of skin, the method comprising: (a) deploying on the skin a sensor system including: (i) a first sensor including a layer of piezoelectric film disposed in thermal and mechanical connection with the first region of skin, the first sensor providing a sensing signal, (ii) a second sensor including a layer of piezoelectric film disposed in mechanical connection with, but thermally isolated from, a second region of skin, the second sensor providing a reference signal, and (iii) a third sensor including a layer of piezoelectric film disposed in mechanical connection with, but thermally isolated from, a third region of skin, the third sensor providing a gate signal; (b) subtracting the reference signal from the sensing signal to generate a corrected sensing signal and from the gate signal to generate a corrected gate signal; (c) when an amplitude of the corrected gate signal is no greater than a predefined gate threshold value, monitoring the corrected sensing signal to detect at least one variation indicative of a malfunction, and (d) when an amplitude of the corrected gate signal is greater than the predefined gate threshold value, temporarily disregarding variations in the corrected sensing signal.

According to a further feature of the present invention, the at least one variation indicative of a malfunction includes a sequence of two variations occurring between 0.1 seconds and 100 seconds apart.

According to a further feature of the present invention, the at least one variation indicative of a malfunction includes a sequence of two variations occurring between 0.5 seconds and 10 seconds apart.

There is also provided according to the teachings of the present invention, a method for detecting extravasation of a fluid delivered from the tip of a catheter into tissue located under a first region of skin, the method comprising: (a) deploying on the skin a non-invasive sensor system including at least one sensor producing at least one output, the sensor system being operative to identify changes in both subcutaneous interstitial fluid pressure in the first region of skin and a skin temperature; (b) monitoring the at least one output to identify a sequence of variations in the at least one output corresponding to a skin temperature drop followed by a interstitial fluid pressure increase; and (c) generating an alarm condition when the sequence of variations occurs.

According to a further feature of the present invention, the at least one sensor includes at least one measuring sensor and a gate sensor, the gate sensor producing an output indicative of disruptive motion likely to adversely affect an output of the at least one measuring sensor, the method further comprising disregarding the output of the at least one measuring sensor when the output of the gate sensor indicates the occurrence of disruptive motion.

According to a further feature of the present invention, the at least one sensor includes a piezoelectric film primary sensor sensitive simultaneously to variations in interstitial fluid pressure and skin temperature.

According to a further feature of the present invention, the sensor system further includes a piezoelectric film reference sensor insulated so as to be unaffected by variations in the skin temperature, an output from the reference sensor being subtracted from an output from the primary sensor.

There is also provided according to the teachings of the present invention, a system for detecting extravasation of a fluid delivered from the tip of a catheter into tissue located under a first region of skin, the system comprising: (a) a sensor system for non-invasive deployment on the skin, the sensor system including: (i) a first sensor including a layer of piezoelectric film configured to be disposed in thermal and mechanical connection with the first region of skin, the first sensor providing a sensing signal, (ii) a second sensor including a layer of piezoelectric film configured to be disposed in mechanical connection with, but thermally isolated from, a second region of skin, the second sensor providing a reference signal, and (iii) a third sensor including a layer of piezoelectric film configured to be disposed in mechanical connection with, but thermally isolated from, a third region of skin, the third sensor providing a gate signal; and (b) a processing system electrically coupled to the first second and third sensors, the processing system including: (i) a first differencing module configured to subtract the reference signal from the sensing signal to generate a corrected sensing signal, (ii) a second differencing module configured to subtract the reference signal from the gate signal to generate a corrected gate signal, (iii) a comparator module configured to compare a current amplitude of the corrected gate signal with a predefined gate threshold value, and (iv) a monitoring module configured to monitor the corrected sensing signal during periods when the comparator module determines that the corrected gate signal is no greater than the threshold value to detect at least one variation in the corrected sensing signal indicative of a malfunction.

According to a further feature of the present invention, there is also provided a closure device associated with the processing system and with a conduit supplying the fluid to the catheter, the closure device being responsive to the monitoring module to prevent fluid flow through the conduit when the at least one variation in the corrected sensing signal is indicative of a malfunction.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
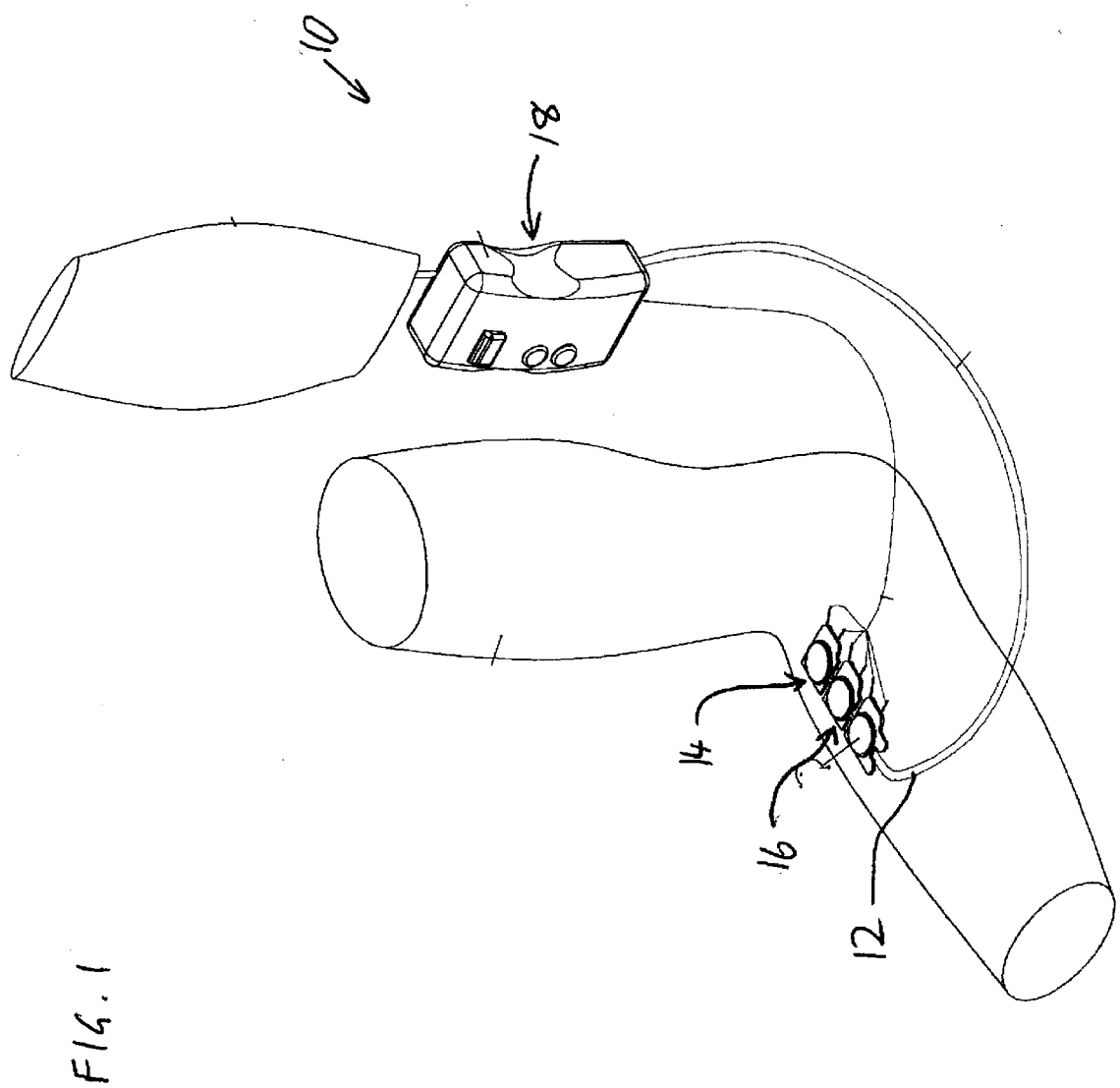
FIG. 1 is a schematic isometric view of a device, constructed and operative according to the teachings of the present invention, for detecting extravasation.

The present invention is a method and device for detecting extravasation.

The principles and operation of methods and devices according to the present invention may be better understood with reference to the drawings and the accompanying description.

By way of introduction, it will be useful to describe the underlying principles of the present invention. Specifically, the present invention employs a non-invasive sensor system deployed on the skin to identify changes in both subcutaneous interstitial fluid pressure and skin temperature in a region of skin above the location where the fluid is intended to be delivered. The system monitors the outputs of the sensor system to identify variations in the aforementioned parameters which satisfy predefined criteria, generating an alarm condition when such variations are found. Preferably, the system monitors the outputs to identify a sequence of variations corresponding to a skin temperature drop followed by a interstitial fluid pressure increase. This pattern of variations, within a given range of parameters, is uniquely distinctive of the occurrence of extravasation, thereby providing much more reliable and sensitive detection than is offered by the existing systems.

Although the method of the present invention can be implemented using a wide range of types of sensors for measuring variations in temperature, variations in interstitial fluid pressure and for detecting patient movement, the invention will be described herein primarily with reference to a non-limiting preferred example in which all sensing is performed using particularly simple and low-cost piezoelectric and pyroelectric sensors which are sensitive both to temperature variations and mechanical deformation.

Referring now to the particular preferred embodiment shown in the drawings, FIGS. 1–5 show the parts of a device, generally designated 10, constructed and operative according to the teachings of the present invention, for detecting extravasation of a fluid delivered from the tip of a catheter 12 into tissue located under a first region 14 of skin. The system is made up essentially of a sensor system 16 for non-invasive deployment on the skin to which a processing system 18 is electrically coupled.

Figure 2:
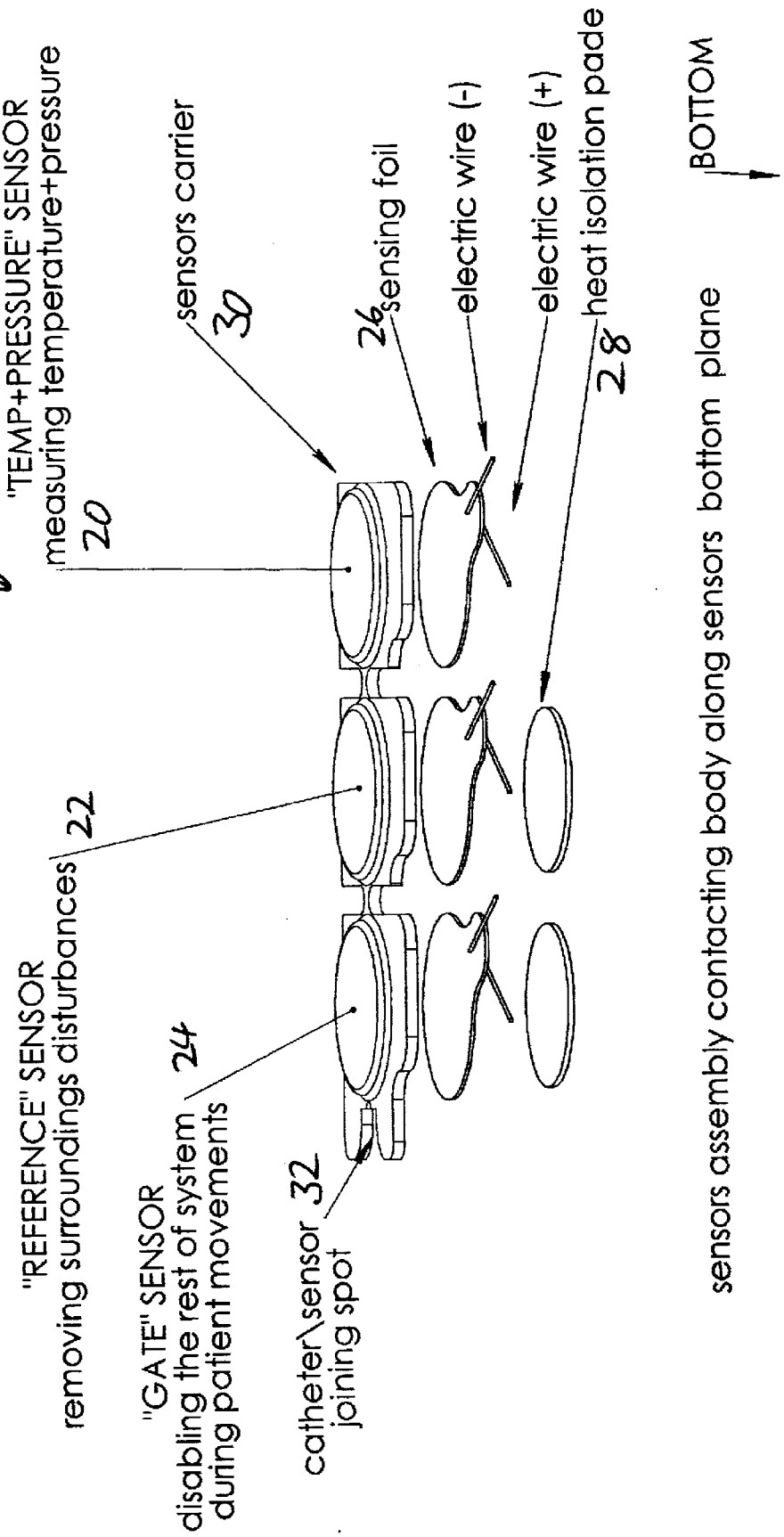
FIG. 2 is an exploded isometric view of a sensor system from the device of FIG. 1.
Figure 3:
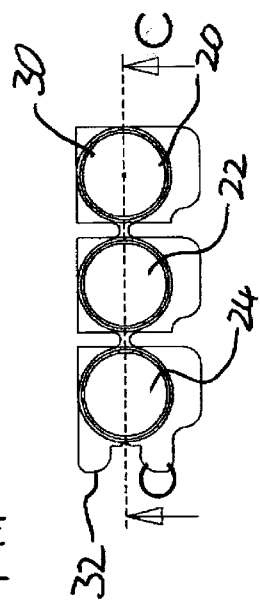
FIG. 3 is a plan view of the sensor system of FIG. 2.
Figure 4:
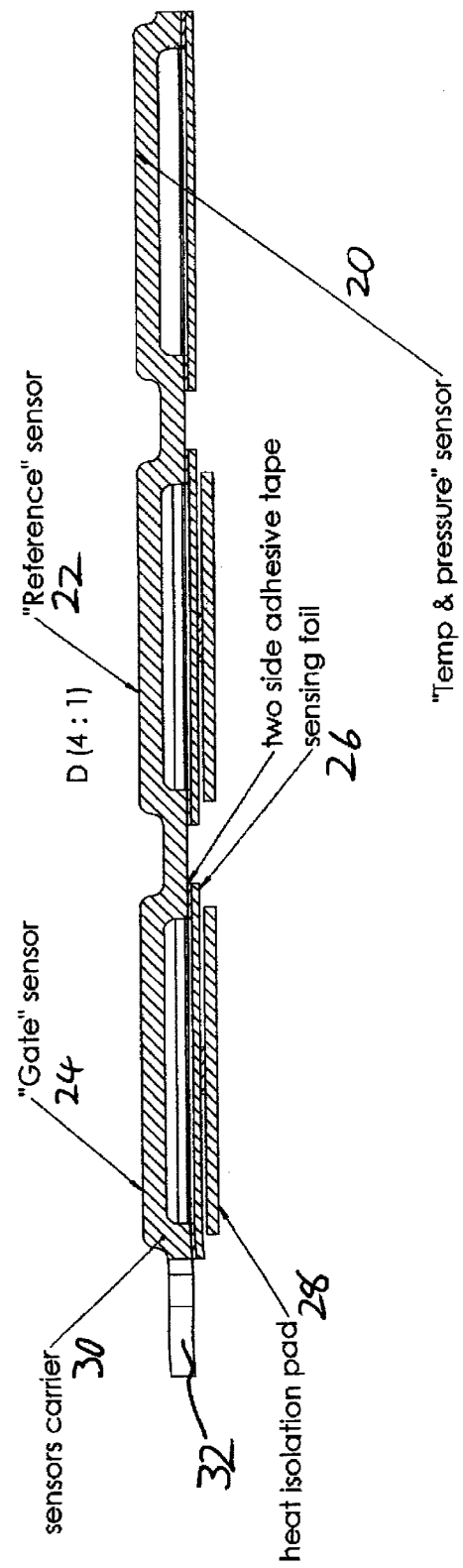
FIG. 4 is a longitudinal cross-sectional view taken through the sensor system of FIG. 2.

Details of sensor system 16 are shown in FIGS. 2–4. Specifically, sensor system 16 preferably includes a first "sensing" sensor 20, a second "reference" sensor 22, and a third "gate" sensor 24, each disposed over a region of the skin. In the preferred embodiment shown here, each sensor includes a layer 26 of piezoelectric film or foil, typically of PVDF. Sensing sensor 20 has layer 26 configured to be disposed in thermal and mechanical connection with the first region of skin opposite the end of the needle or catheter tube where the fluid is to be released. Second and thirds sensors 22 and 24 are configured to overlie adjacent regions of skin in mechanical connection with the skin, but thermally isolated therefrom. The thermal isolation is preferably achieved by providing an insulating pad 28. All three sensors are preferably protected by housings 30, typically of rigid plastic material, which are advantageously integrally formed as a single unit. By arranging the three sensors in a row, and adding alignment features 32 for positioning at the point of entry of the catheter through the skin, the structure is advantageously configured such that sensing sensor 20 will inherently be positioned opposite the end of the catheter for a predefined fluid delivery system.

The properties of the piezoelectric film sensors are such that they generate an electric signal between their electrodes when exposed to either variations in temperature (pyroelectric properties) or mechanical deformation (piezoelectric properties). Thus, sensing sensor 20 generates a signal either when the skin temperature drops or when the interstitial fluid pressure increases, causing local swelling which deforms the piezoelectric layer, both of which are symptoms of extravasation. Spurious electric signals, however, may be generated as a result of electromagnetic interference/background noise or patient motion unrelated to extravasation. The use of three sensors as described allows the present invention to avoid false alarms from either of these sources, as will be detailed below.

Specifically, it should be noted that the unwanted signals may be subdivided into two general categories: background noise such as power supply transients, magnetic and electrostatic and RF EM fields which are substantially continuous and which generally affects all of the sensors simultaneously and identically; and patient motion which is sporadic, but which, depending upon the type of motion, may cause variations with slight time delays between the sensors. The present invention preferably addresses these two types of unwanted signal separately.

Thus, a reference signal from reference sensor 22 is subtracted from both the sensing signal from sensor 20 and from the gate signal from sensor 24. This is effective to cancel out the background noise, as well as any component of movement-related noise which affects all of the sensors simultaneously and equally. The only remaining unwanted signals result from certain types of patient motion which affect the different sensors out of phase, i.e., with a certain time lag. The presence of such out-of-phase motion-related signals is identified by comparing the magnitude of the corrected gate signal, i.e., after subtraction of the reference signal, with a predefined threshold value. When the predefined value is exceeded, movement-related readings are indicated. Since the movement is transient, the system may safely disregard the sensing signals for the period that movement-related noise is detected, subsequently returning to its normal monitoring mode.

In structural terms, it will be appreciated that processing system 18 may be implemented in a number of forms to perform the required functions. Specifically, processing system 18 may be implemented as any type of processor known for performing the various functions described herein. This includes purpose hardware, either analogue or digital, configured for performing the recited functions, multipurpose processors operating with appropriate software, and hardware-software combinations referred to as "firmware". The various functions which will be described herein attributed to processing system 18 may in fact be subdivided between a number of separate processors, or may be performed by a single processor. The various functions described may all readily be implemented by one ordinarily skilled in the art. Accordingly, the processor will be described herein in functional terms only, the selection of specific hardware and software being well within the capabilities of an ordinarily skilled technician.

Figure 5:
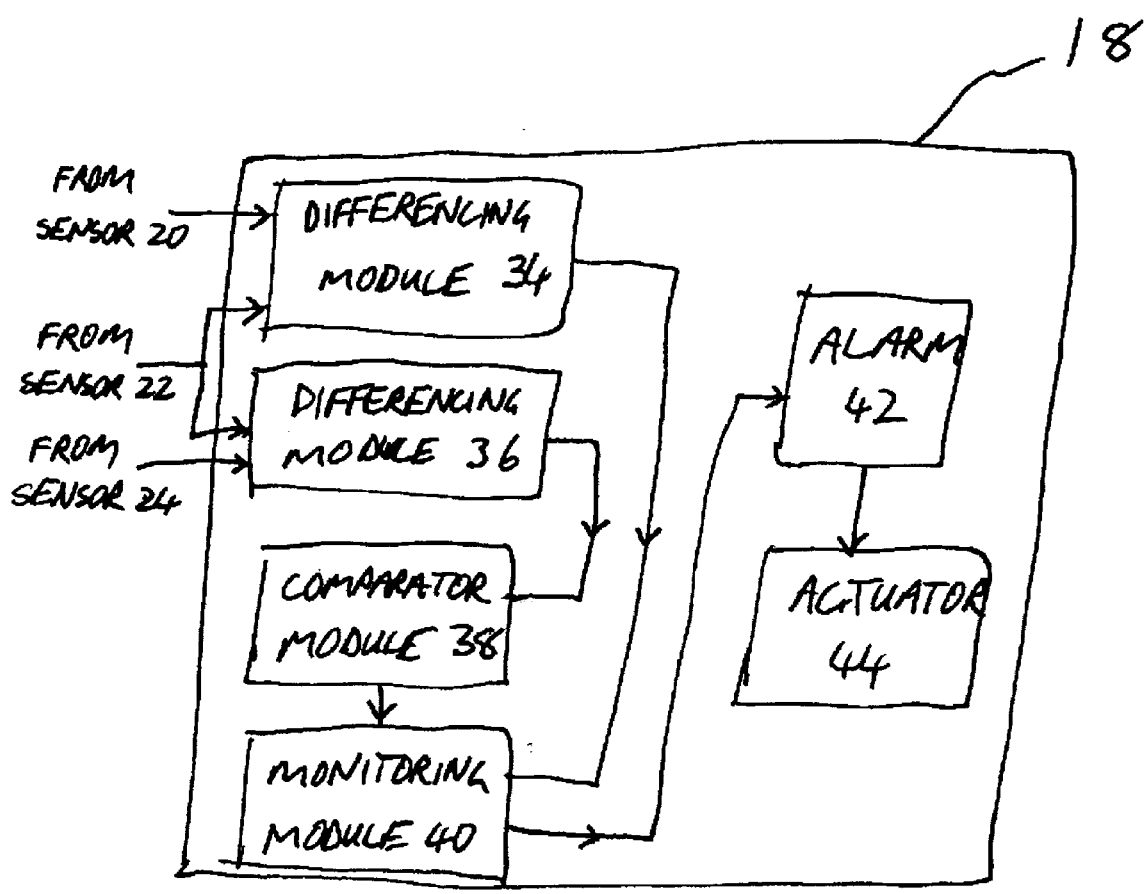
FIG. 5 is a schematic representation of the main functional components of a processing system from the device of FIG. 1.

Thus, with reference to FIG. 5, processing system 18 includes: a first differencing module 34 configured to subtract the reference signal from the sensing signal to generate a corrected sensing signal, a second differencing module 36 configured to subtract the reference signal from the gate signal to generate a corrected gate signal, a comparator module 38 configured to compare a current amplitude of the corrected gate signal with a predefined gate threshold value, and a monitoring module 40 configured to monitor the corrected sensing signal during periods when the comparator module determines that the corrected gate signal is no greater than the threshold value to detect at least one variation in the corrected sensing signal indicative of extravasation. Preferably, processing system 18 also includes a visible and/or audible alarm 42 which is activated in the event that extravasation is detected, and optionally also an actuator 44 associated with the fluid delivery device and configured to interrupt fluid delivery when an alarm occurs.

Figure 6:
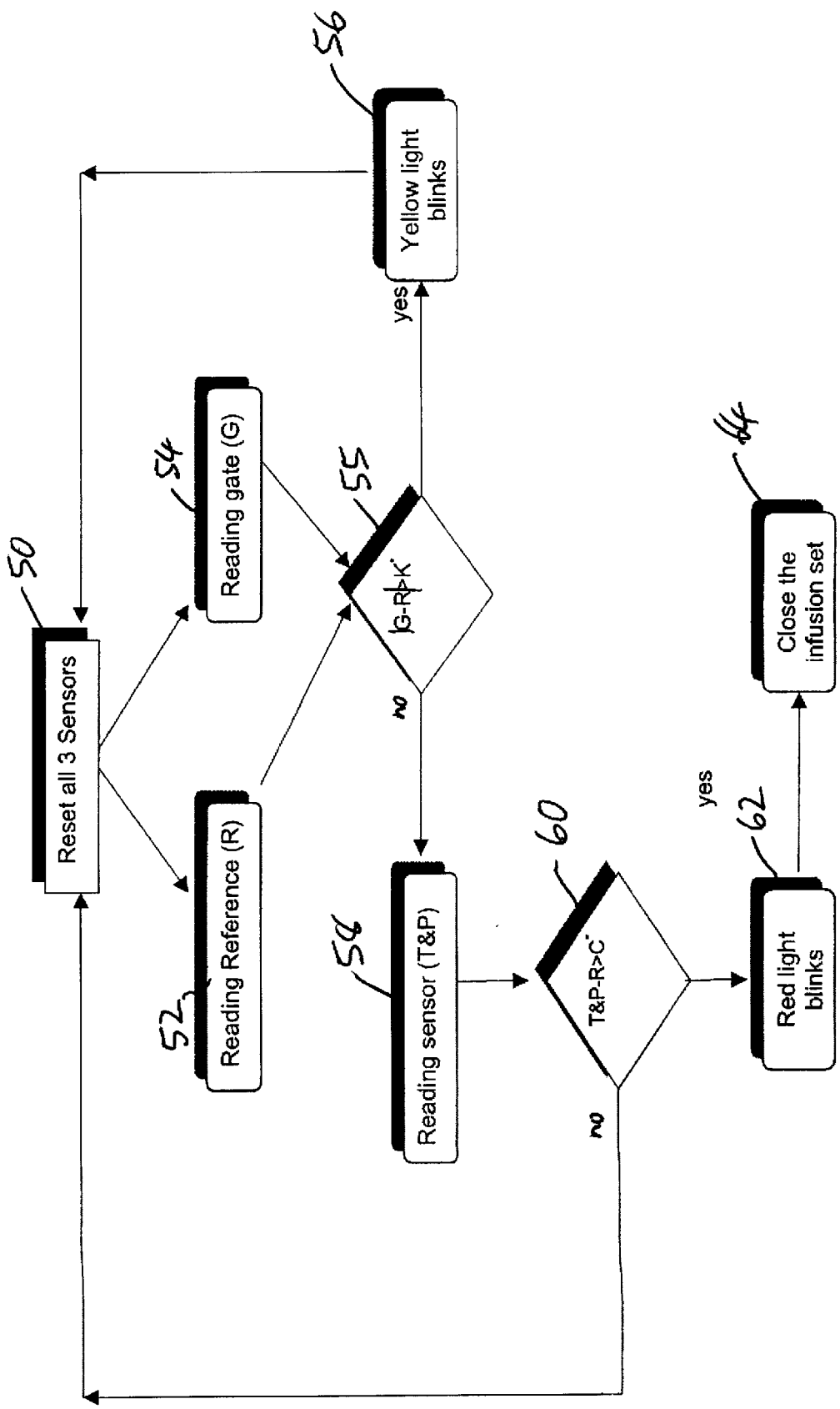
FIG. 6 is a flow diagram illustrating a first mode of operation of the device of FIG. 1.

Turning now to FIG. 6, this presents a basic implementation of the present invention which illustrates the use of three sensors for noise-elimination according to the teachings of the present invention. Thus, the sensors are first reset (step 50), typically by discharging any capacitive charge which has accumulated on the film, and the signals from the reference sensor 22 and the gate sensor 24 are read (steps 52 and 54). The magnitude of the difference between these signals is then compared with a predefined threshold K (step 55). If it exceeds the threshold, this indicates that patient movement is currently disrupting the measurements. Accordingly, the process returns to step 50, optionally providing a "disrupted measurement" signal such as by illuminating a lamp (step 56). Under "normal" conditions, when threshold K is not exceeded, the system proceeds to step 58. Here, sensing sensor 20 is read and the difference between the sensing signal and the reference signal is monitored for indications of extravasation (step 60). In the basic implementation represented here, step 60 is performed as a second simple threshold comparison with a predefined value C. If extravasation is detected, an alarm signal is generated (step 62) and, optionally, the fluid delivery is automatically interrupted (step 64).

In most cases, however, in order to reduce the likelihood of false alarms to near zero levels, and in order to increase sensitivity, the simple threshold comparison of step 60 is replaced by a more sophisticated signal analysis. Specifically, the system preferably monitors the corrected sensing output in order to identify a pattern of time variation indicative of a drop in skin temperature followed by an increase in subcutaneous interstitial fluid pressure.

Figure 7:
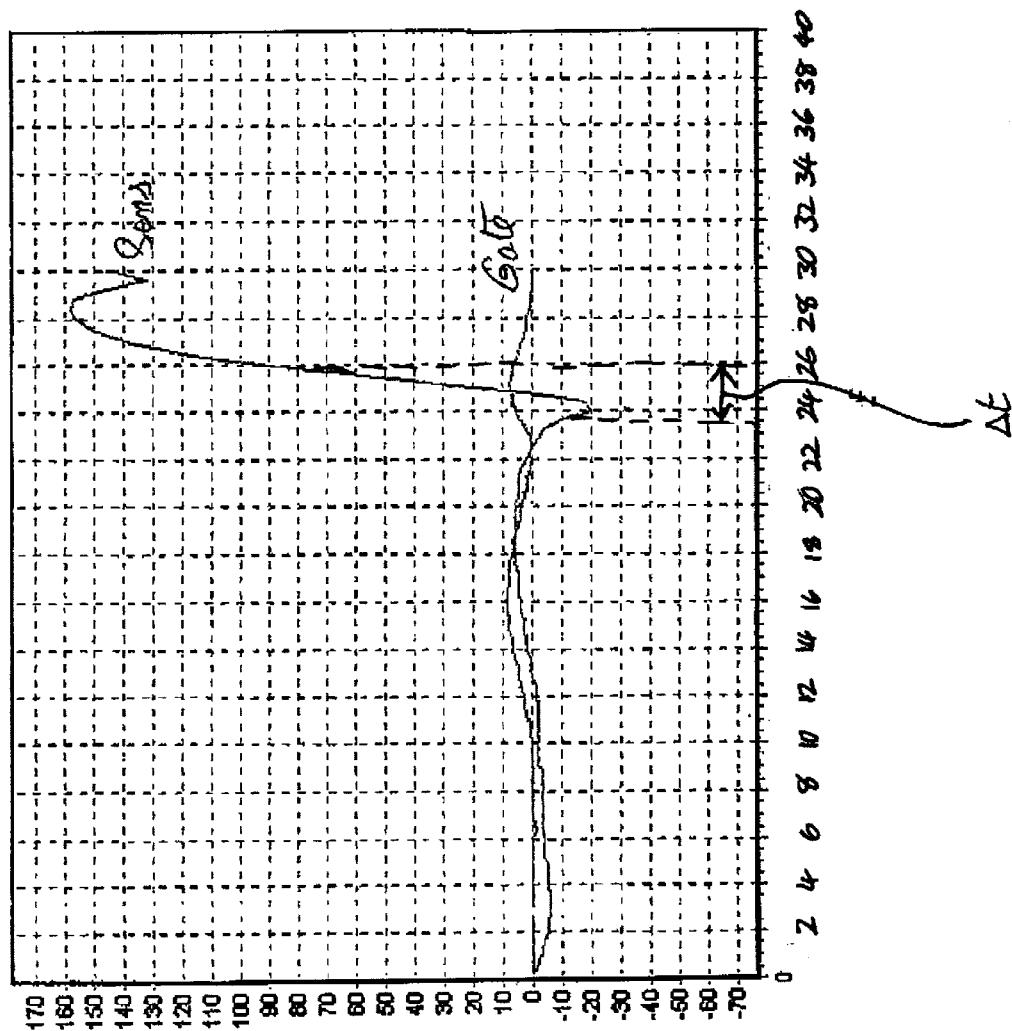
FIG. 7 is a plot of corrected sensor signals illustrating a sequence of variations indicative of extravasation according to a second preferred mode of operation of the present invention.

FIG. 7 shows the corrected sensor and gate signals illustrating a sequence of variations in temperature and pressure indicative of occurrence of extravasation. In this preferred implementation, the sensor is configured such that temperature drop and increased pressure result in opposite variations in voltage on the sensor, thereby rendering identification of the separate peaks particularly straightforward. The corrected sensing signal here clearly shows a first negative peak (minimum) indicative of a temperature drop, followed by a positive peak (maximum) indicative of a subcutaneous interstitial fluid pressure increase. The measurement of the delay between the variations may be evaluated by a wide range of known algorithms for signal processing of this type. Examples include, but are not limited to: time between maximum gradients; time between half-maximum-amplitude measurements; and peak-to-peak time.

The range of delays between the two variations which is considered indicative of extravasation preferably lies within the range from 0.1 seconds to 100 seconds. More preferably, the criteria may be set as $0.5 \text{ s} \leq \Delta t \leq 10 \text{ s}$. Typically, the actual measured value of $\Delta t$ is thought to lie in the range of 2–5 seconds. Clearly, if sensors with significantly differing response times to variations in temperature and pressure are employed, a preprocessing correction will be required prior to application of the time delay criteria.

Figure 8:
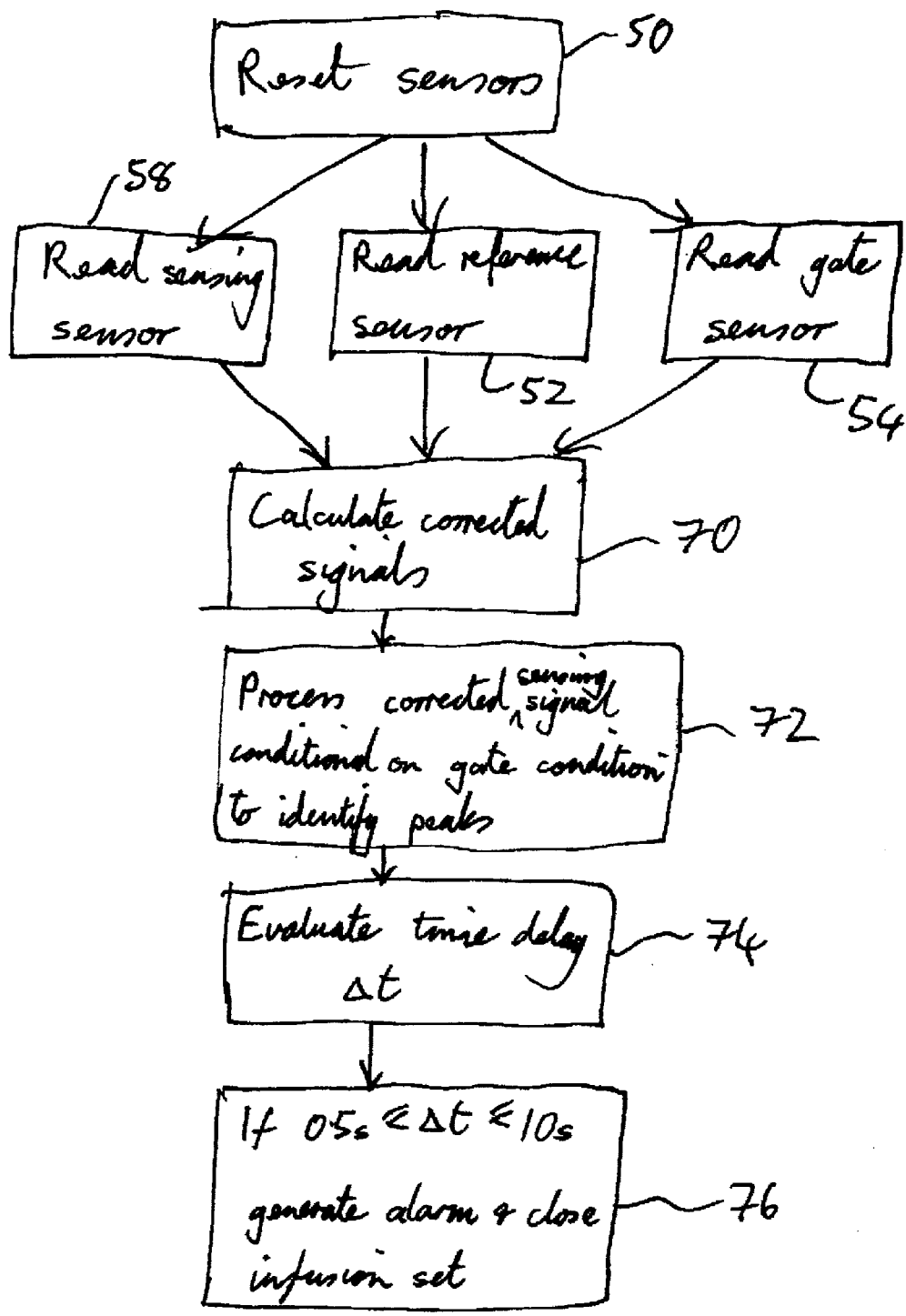
FIG. 8 is a flow diagram illustrating the second mode of operation of the device of FIG. 1.

The operation of the system according to this preferred implementation is illustrated in FIG. 8. After initially resetting the sensors (step 50) and reading each sensor (steps 58, 52 and 54) the corrected signals are calculated (step 70). These signals are then processed 72 to detect peaks in the sensing signal while discarding readings taken while the corrected gate sensor exceeds the gate threshold. Once two peaks of at least a given magnitude are detected, the time delay between them is evaluated 74. If the time delay satisfies the predefined criteria, for example here 0.5 s≦Δt≦10 s, an alarm is generated and optionally the infusion set is automatically closed (step 76).

Finally, it should be appreciated that the invention is not limited either to the specific type or number of sensors in the preferred example thus far. By way of illustration, it should be noted that sensing sensor 20 may be replaced by two separate sensors, one of which is sensitive only to variations in pressure while the second in sensitive only to variations in temperature. Furthermore, while the pressure sensor is necessarily deployed opposite the end of the catheter from which fluid is released, the temperature sensor may be mounted at an alternative location in which the skin temperature is also influenced by the rate of fluid supply. Thus, by way of a particular example, a temperature sensor may advantageously be deployed immediately adjacent to the point of entry of the catheter through the skin. The skin temperature of this region is directly affected through heat conduction effects by the fluid flow rate through the catheter. In the event of extravasation, a change in fluid flow impedance results in a change in the rate of flow, causing a corresponding temperature change adjacent to the point of entry of the catheter. Sensing of variations in the subcutaneous interstitial fluid pressure are detected by a separate sensor in a manner analogous to that described above.

It will be appreciated that the above descriptions are intended only to serve as examples, and that many other embodiments are possible within the spirit and the scope of the present invention.

What is claimed is:

1. A method for detecting extravasation of a fluid delivered from the tip of a catheter into tissue located under a first region of skin, the method comprising:
   (a) deploying on the skin a sensor system including:
      (i) a first sensor including a layer of piezoelectric film disposed in thermal and mechanical connection with the first region of skin, the first sensor providing a sensing signal,
      (ii) a second sensor including a layer of piezoelectric film disposed in mechanical connection with, but thermally isolated from, a second region of skin, the second sensor providing a reference signal, and
      (iii) a third sensor including a layer of piezoelectric film disposed in mechanical connection with, but thermally isolated from, a third region of skin, the third sensor providing a gate signal;
   (b) subtracting the reference signal from the sensing signal to generate a corrected sensing signal and from the gate signal to generate a corrected gate signal;
   (c) when an amplitude of the corrected gate signal is no greater than a predefined gate threshold value, monitoring the corrected sensing signal to detect at least one variation indicative of a malfunction; and
   (d) when an amplitude of the corrected gate signal is greater than the predefined gate threshold value, temporarily disregarding variations in the corrected sensing signal.

2. The method of claim 1, wherein said at least one variation indicative of a malfunction includes a sequence of two variations occurring between 0.1 seconds and 100 seconds apart.

3. The method of claim 1, wherein said at least one variation indicative of a malfunction includes a sequence of two variations occurring between 0.5 seconds and 10 seconds apart.

4. A method for detecting extravasation of a fluid delivered from the tip of a catheter into tissue located under a first region of skin, the method comprising:
   (a) deploying on the skin a non-invasive sensor system including at least one sensor producing at least one output, said sensor system being operative to identify changes in both subcutaneous interstitial fluid pressure in said first region of skin and a skin temperature;
   (b) monitoring said at least one output to identify a sequence of variations in said at least one output corresponding to a skin temperature drop followed by a interstitial fluid pressure increase; and
   (c) generating an alarm condition when said sequence of variations occurs.

5. The method of claim 4, wherein said at least one sensor includes at least one measuring sensor and a gate sensor, said gate sensor producing an output indicative of disruptive motion likely to adversely affect an output of said at least one measuring sensor, the method further comprising disregarding the output of said at least one measuring sensor when said output of said gate sensor indicates the occurrence of disruptive motion.

6. The method of claim 4, wherein said at least one sensor includes a piezoelectric film primary sensor sensitive simultaneously to variations in interstitial fluid pressure and skin temperature.

7. The method of claim 6, wherein said sensor system further includes a piezoelectric film reference sensor insulated so as to be unaffected by variations in the skin temperature, an output from said reference sensor being subtracted from an output from said primary sensor.

8. A system for detecting extravasation of a fluid delivered from the tip of a catheter into tissue located under a first region of skin, the system comprising:
   (a) a sensor system for non-invasive deployment on the skin, the sensor system including:
      (i) a first sensor including a layer of piezoelectric film configured to be disposed in thermal and mechanical connection with the first region of skin, the first sensor providing a sensing signal,
      (ii) a second sensor including a layer of piezoelectric film configured to be disposed in mechanical connection with, but thermally isolated from, a second region of skin, the second sensor providing a reference signal, and
      (iii) a third sensor including a layer of piezoelectric film configured to be disposed in mechanical connection with, but thermally isolated from, a third region of skin, the third sensor providing a gate signal; and
   (b) a processing system electrically coupled to said first second and third sensors, said processing system including:
      (i) a first differencing module configured to subtract the reference signal from the sensing signal to generate a corrected sensing signal,
      (ii) a second differencing module configured to subtract the reference signal from the gate signal to generate a corrected gate signal, (iii) a comparator module configured to compare a current amplitude of the corrected gate signal with a predefined gate threshold value, and (iv) a monitoring module configured to monitor the corrected sensing signal during periods when said comparator module determines that said corrected gate signal is no greater than said threshold value to detect at least one variation in said corrected sensing signal indicative of a malfunction.

9. The system of claim 8, further comprising a closure device associated with said processing system and with a conduit supplying the fluid to the catheter, said closure device being responsive to said monitoring module to prevent fluid flow through the conduit when said at least one variation in said corrected sensing signal is indicative of a malfunction.

\* \* \* \* \*

UNITED STATES PATENT AND TRADEMARK OFFICE
CERTIFICATE OF CORRECTION

PATENT NO.    : 6,425,878 B1
DATED         : July 30, 2002
INVENTOR(S)   : Shekalim It is certified that error appears in the above-identified patent and that said Letters Patent is hereby corrected as shown below:

<u>Title page,</u>
Item [75], the inventors name is mistakenly shown as "Avraharn" when it should be
-- Avraham --

Signed and Sealed this

Tenth Day of December, 2002

JAMES E. ROGAN
*Director of the United States Patent and Trademark Office*